US011406726B1

(12) United States Patent
Yu

(10) Patent No.: US 11,406,726 B1
(45) Date of Patent: Aug. 9, 2022

(54) MULTIFUNCTION GERMICIDAL APPARATUS AND METHOD

(71) Applicant: Simon Siu-Chi Yu, Oakland, CA (US)

(72) Inventor: Simon Siu-Chi Yu, Oakland, CA (US)

( * ) Notice: Subject to any disclaimer, the term of this patent is extended or adjusted under 35 U.S.C. 154(b) by 0 days.

(21) Appl. No.: 17/478,251

(22) Filed: Sep. 17, 2021

Related U.S. Application Data

(60) Provisional application No. 63/206,151, filed on Jan. 29, 2021, provisional application No. 63/258,335, filed on Apr. 26, 2021.

(51) Int. Cl.
*A61L 2/10* (2006.01)
*A61L 2/20* (2006.01)

(52) U.S. Cl.
CPC ................. *A61L 2/10* (2013.01); *A61L 2/202* (2013.01); *A61L 2202/11* (2013.01)

(58) Field of Classification Search
CPC ......... A61L 2/10; A61L 2/202; A61L 2202/11
See application file for complete search history.

(56) References Cited

U.S. PATENT DOCUMENTS

2006/0008379 A1* 1/2006 Mielnik .................. A61L 2/208 422/32
2009/0314308 A1* 12/2009 Kim .......................... A61L 2/24 134/1

* cited by examiner

*Primary Examiner* — Sean E Conley
(74) *Attorney, Agent, or Firm* — Lyman Moulton, Esq.; Moulton Patents, PLLC

(57) ABSTRACT

The disclosed Multi-function Germicidal Apparatus and Method, is an elevation actuator equipped mobile floor-standing air convection system including an electromagnetic radiation oscillating head mounted dish with zoom and focusable UV beam projectors which sweep across a horizontal plane to inactivate airborne pathogens. An open end germicidal chamber behind an open center nozzle is equipped with multi-wavelength UV lights to inactivate passing pathogens and irradiate TIO2 coated charge plates to generate hydroxyl radicals. A fan pushes contaminated air through a chamber discharging remnant pathogens and air mixed through a nozzle to create a high velocity air mixture farther away from the opening. An oscillating and focused UV beam forms a tubular shaped virtual cage encircling exiting pathogens for continuous inactivation. Convection forced pathogens disperse to the floor are picked up by a floor fan and sent back to a chamber and UV beams for repeating inactivation.

20 Claims, 12 Drawing Sheets

MULTIFUNCTION GERMICIDAL APPARATUS AND METHOD

CROSS REFERENCE

Applicant claims priority to the Provisional patent application 63/206,151 filed Jan. 29, 2021 titled Multifunction Germicidal Apparatus and Method and to the Provisional patent application 63/258,335 filed Apr. 26, 2021 under the same title and also by Simon Siu-Chi Yu which are both incorporated entirely into the present non-provisional patent application.

BACKGROUND

UV tube lamps to disinfect pathogens. They are heavy, low efficiency, have a short service lamp life, contain toxic Mercury, require constant cleaning of the lamp reflector and require trained trades staff to install on seven feet tall walls or mount on ceilings that are very costly on installation and maintenance. These germicidal fixtures use an array of shutters to direct UV upward to avoid irradiating the occupants. The disadvantage of tube lamps is that energy attenuation follows an inverse-square-law. Distances of ten feet from the UV light source leave only one percent. They require multiple unit installations to make up the deficiency. The natural air convection rate is very small and slow. Some models are equipped with a circulation fan, but often some locations in a room are completely unaffected and give some false security to the occupants. There have been no products available as original equipment or as an aftermarket to address this problem.

An apparatus that solves the output attenuation and the active convection apparatus enables disinfection of a large area without restriction by the inverse-square-law. However, there have been no products available as original equipment or as an aftermarket to address this problem either.

SUMMARY OF THE INVENTION

This invention discloses a complete clean air solution in two steps to protect occupants in a house. First step is preventing pathogens from being brought in from the outside. A second step is continuously disinfecting the house with occupants present in safe manner. Both steps share some identical components but achieve different results.

The Multi-function Germicidal Apparatus and Method is directed to using a hand carrying portable high velocity high volume air blasting cannon and a mobile floor-station to disinfect airborne and surface viruses, and bacteria. The hand carrying personal disinfection cannon further converts to a hand free operating floor-stand for intercepting germs via an air blasting station. The invention further discloses an active convection upper room germicidal system equipped with solid state semiconductor zoom and focusable UV projectors. The disclosure shoots a plurality of focused beams sweeping across a horizontal plane to effectively disinfect viruses over long range. The air blasting station further uses parametric ultrasound speaker arrays to destroy pathogens in wide areas.

The hand carried, cordless battery operated high velocity high volume air blasting cannon blasts high velocity air up to 110 mile per hour at 600 cubic foot per minute. The high momentum air is capable of dislodging dust, pollen, bacteria, and viruses that have clung on a person's skin and clothing.

The high velocity high volume air blasting cannon comes equipped with a germicidal chamber on an exit side of the cannon's high air velocity fan. Inside the chamber, a group of germicidal modules are configured to inactivate the passing pathogens while being pushed out from the fan.

The module inside the chamber includes an ozone generator for blasting a person. The ozone riding on the high velocity air striking a person causes dislocation of pathogens, and remnants of pathogens impacted by high momentum ozone quickly oxidized and inactivated.

The module inside the chamber also includes a multi wavelength UV LED (light Emit Diodes) light. The UV light is configured to produce hydroxyl radicals with passing water molecules from ambient air while also irradiating the TIO2 semiconductor coating to generate a photocatalysis process.

The module inside the chamber additionally includes a Hydroxyl generator for blasting a person. The Hydroxyl radicals riding on the high velocity air impacts a person causing dislodge of pathogens, and remnant of pathogens impacting by high momentum Hydroxyl radicals which are quickly oxidized and inactivated.

The module inside the chamber further includes a bipolar ions generator for further blasting the person. The ions riding on the high velocity air impact a person and cause a dislocation of pathogens, and remnant of pathogens impacted by high momentum ions which are quickly oxidized and inactivated.

The module inside the chamber yet includes a photocatalysis converter. The pathogens being quickly inactivated on the TIO2 coated charge plates are irradiating by the multi wavelength UV light and turned into harmless molecules and subsequently blasted out from the chamber.

The high velocity, high volume air blasting cannon further equips a user with a set of foldable blades installed on an oscillating open center motorized on a turntable via hinges. A set of zooming and focusable UV LED or UV Laser diodes are mounted on the blades. A set of red 650 nm laser diodes are mounted on the tip of the blades to guide the user visualizing the target being irradiating for disinfection because the UV ray is invisible.

Other advantages of the invention include a rapid conversion of the air blasting cannon to a wheeled pole floor-stand configured to intercept germs via an air blasting station. An elevation, vertical motion linear actuator installed on the floor-stand provides an accent and a decent motion to the air blasting cannon.

A hinge connects the vertical motion linear actuator with a baseboard holding a motorized turntable. A bow motion actuator connects to the baseboard. The bow motion linear actuator moves up and down to move the board into a bow motion.

A turntable is sandwiched in between a baseboard and a docking board in a multi motion docking assembly that securely holds the cannon in place from falling. A synchronized AC motor is anchored on the baseboard while the motor leverage link drives the upper mount docking plate to cause the cannon to move in a sweeping motion. The synchronized AC motor automatically reverses its direction when the cannon gets stuck with another object.

Another advantage is an automation embodiment of a touch-less and active infrared sensor to eliminate cross contamination. Another advantage of the present embodiment is intercepting germs via an air blasting station from a higher elevation and achieving a surface disinfection.

Another advantage of an embodiment of the present disclosure is converted germs intercepted by a wheeled air blasting station ideally placed behind a front entrance door. Once activated, the air blasting cannon blasts an occupant and blows the resulting contaminated air to the exterior from the inside of a house.

Yet another advantage of an embodiment of the invention is a variance configured as a multi-function germicidal station, operable via an occupant present in a room by a fully automated operation selective disinfection mode to best suit a particular and predetermined application.

The multi-function germicidal station is ideally suited for upper room germicidal operations comprising a wheeled floor-stand mount with an elevation actuator to provide accent and decent motion to adjust the external dish head and conical nozzle germicidal assembly to clear occupants' heads for safety.

In an embodiment, a multi motion docking assembly comprise a motorize turntable, a top side of the table connected to a docking plate, and a bottom side connected to a baseboard. Furthermore, the upper room germicidal station further comprises a push fan configured to propel a high volume of air through the opening of an oscillating external dish head with a conical nozzle germicidal assembly.

Embodiments include the external germicidal dish head mounts with an array of zoom and focusable LED UV projectors or UV Laser diodes for pathogen inactivation and a set of red laser diodes mounted on the edge of the dish head to visually guide a user to the intended target area.

An internal germicidal chamber comprises multiple modules to be selected for specific applications including an ozone generator, a hydroxyl radical generator, multi wavelength UV light source, TIO2 photocatalysis processor bipolar ions generator and a parametric ultrasound speakers array.

Another advantage of the invention comprises a long range active air convection configured to repeatedly circulating air from its floor stand to a far-end from the germicidal station stand. The decontaminated air blasting from ceiling level in an upper room quickly disperses to a lower floor level and is picked up and sent back for repeating disinfection.

Yet another advantage of the invention discloses a tubular shaped virtual UV beam disinfection cage. The virtual cage is created when the zoom and focused UV LED or laser diode projection UV beams around the external dish head conical nozzle germicidal assembly. The beams effectively encircling the pathogens discharging from the open center in the form of co-extrusion fashion are continuously stroked by the UV beams effect quick inactivation.

Yet in another embodiment, an array of parametric ultrasound speakers are mounted on the external germicidal dish head bombarding the pathogens on air and solid surfaces from their cavitation and acoustic energy.

Another advantage of an embodiment is an array of parametric ultrasound speakers mounted on the interior side of the air delivery elbow. The speakers are facing the oncoming air stream. The ultrasound propagates in opposition direction causing the remnant pathogens which missed the internal germicidal chamber in spinning motion against the interior wall length of flexible air duct which will further weakens the strength of remaining pathogens.

Yet another embodiment advantage is active noise canceling circuitry to reduce the fan noise in a room. Yet another advantage is the system can be linked to a wireless operation from a remote location.

Figure 1:
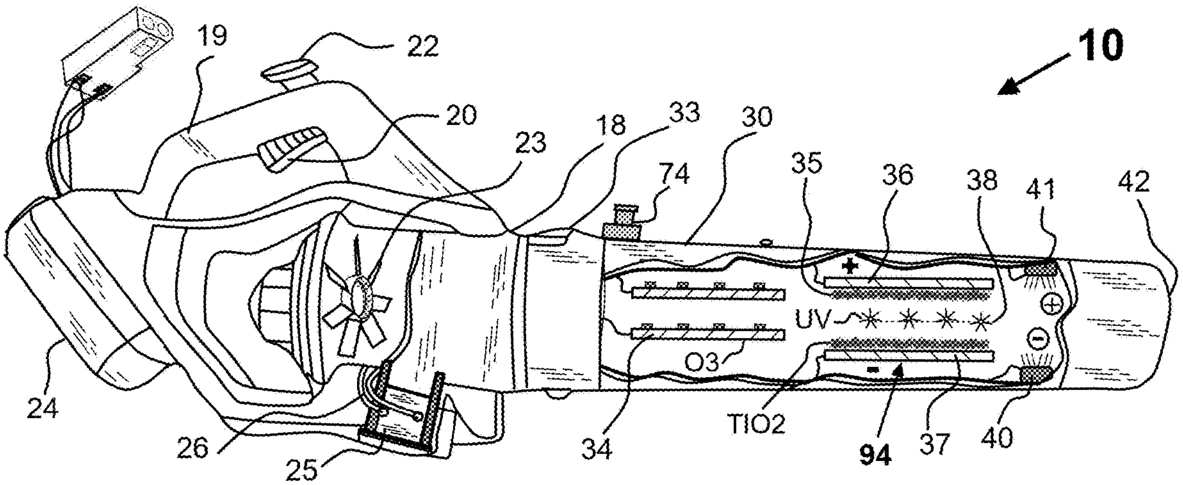
FIG. 1 is a plan perspective view of a battery operated cordless hand carrying high velocity high volume air blasting cannon showing some internal components, in accordance with an embodiment of the present disclosure.

Throughout the description, similar reference numbers may be used to identify similar elements depicted in multiple embodiments. Although specific embodiments of the invention have been described and illustrated, the invention is not to be limited to the specific forms or arrangements of parts so described and illustrated. The scope of the invention is to be defined by the claims appended hereto and their equivalents.

DETAILED DESCRIPTION

Reference will now be made to exemplary embodiments illustrated in the drawings and specific language will be used herein to describe the same. It will nevertheless be understood that no limitation of the scope of the disclosure is thereby intended. Alterations and further modifications of the inventive features illustrated herein and additional applications of the principles of the inventions as illustrated herein, which would occur to one skilled in the relevant art and having possession of this disclosure, are to be considered within the scope of the invention.

FIG. 1 is the multi-function cordless hand carrying high velocity high volume air blasting cannon 10 that equipped with fan and motor 23 moves massive amount of air into germicidal chamber 30 which houses a set of modules including ozone generating ceramic plates 34, a set of titanium oxide TIO2 coating 35 on surface of charge plate 36, 37, an array of multi wavelength UV LED 38 irradiate the surfaces of TIO2 35 causing creation of hydroxyl when passing air carry water vapor, also bipolar ions generator 40, 41. An exterior mounted high voltage 3500 V operates at 16 kHz inverter 25 mounted on the cannon body 18 provides power through high voltage cable 26 to ozone plates 34. A handle 19, air speed control switch 20, module selection switch 22 and a battery 24 are conveniently arranged around the body 18. The chamber 30 attached to a quick release adapter 33 for ease of maintenance of the chamber 30.

In operation, with the switch 20 triggered, fan 23 pushes air passing the modules, if ozone module 34 is selected, the activated oxygen (O3) 60 riding on the air at speed of 110 mph rushing out via nozzle 42 can reach thirty feet for disinfection. If multi wavelength UV light module 38 is selected, hydroxyl radicals (OH) 70 riding on the air at speed of 110 mph rushing out via nozzle 42, because hydroxyl 70 has a very short life time on air about 2 seconds, the hydroxyl 70 inactivate most of the pathogens before it reach thirty feet travel. For higher production of hydroxyl 70, charge plates module 36, 37 are selected in combination with UV light module 38 and TIO2 coaling 35 to effect photocatalysis for fast inactivation of pathogens 54. If bipolar ions module 40, 41 are selected, the exiting negative ions attract to positively charged airborne particles and positive ions attract to negatively charged airborne particulates make them too heavy stay on air and participated to ground quickly. This description is in accordance with an embodiment of the present disclosure.

Figure 1A:
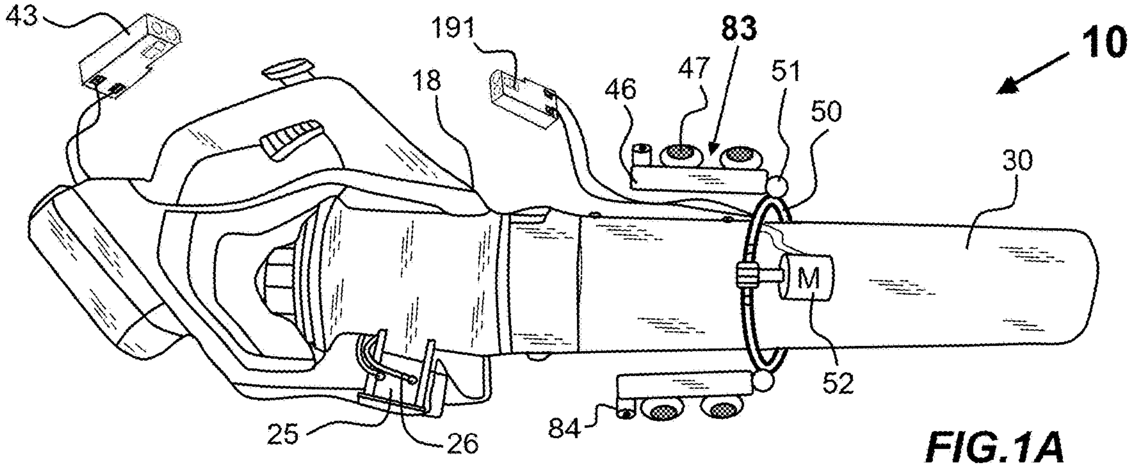
FIG. 1A is a plan perspective view of a battery operated cordless hand carrying high velocity high volume air blasting cannon showing the oscillating surface mounted external foldable blades germicidal assembly with UV projectors mounted on the blades; the blades are in folded not in use position, in accordance with an embodiment of the present disclosure.
Figure 1B:
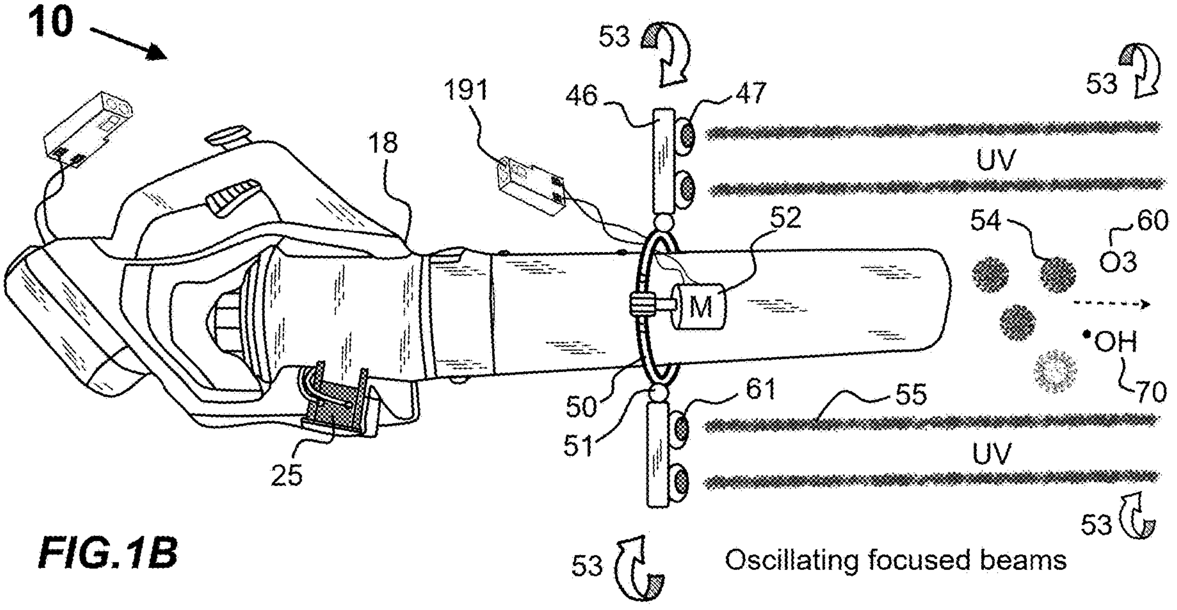
FIG. 1B is a plan perspective view of a battery operated cordless hand carrying high velocity high volume air blasting cannon showing the oscillating surface mounted external foldable blades germicidal assembly, blades are in fully unfolded position ready for use, in accordance with an embodiment of the present disclosure.
Figure 10:
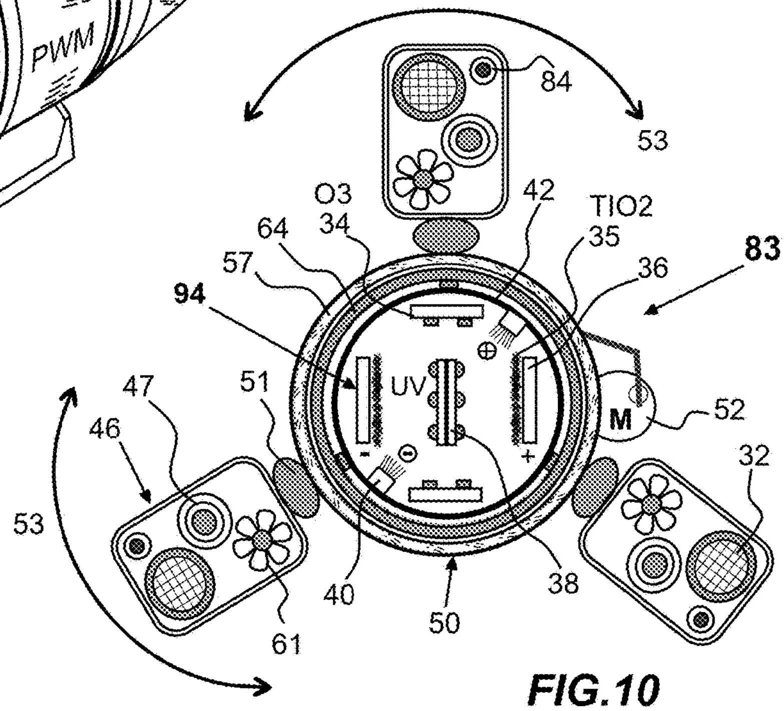
FIG. 10 is a front view of a multi-function battery operated cordless hand carrying high velocity high volume air blasting cannon showing unfolded blades mounted with zoom and focusable UV LED and UV laser diodes, array of parametric ultrasound speakers and a motor drives the open center turntable creates oscillation, in accordance with an embodiment of the present disclosure.
Figure 11:
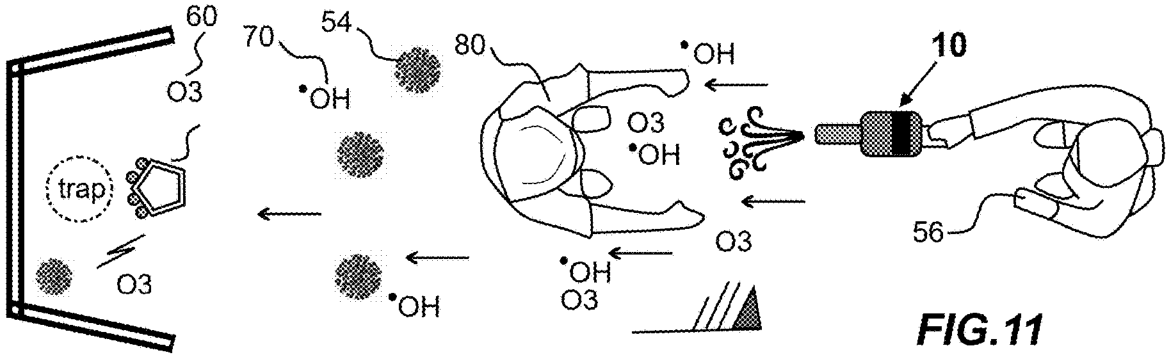
FIG. 11 is overhead view of a multi-function hand carrying high velocity high volume air blasting cannon disinfecting a person with treated air. The dislodged pathogens and ozone capture on the rear side via a tent, in accordance with an embodiment of the present disclosure.
Figure 13:
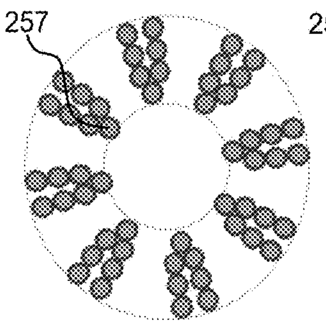
FIG. 13 diagram showing a UV beams pattern irradiated out from external mounted dish head uses in the germicidal station indicate the UV projectors are alternately spaced to minimize pixilation, in accordance with an embodiment of the present disclosure.
Figure 13A:
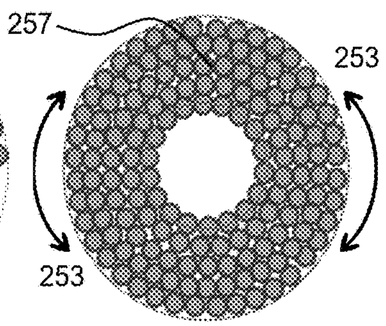
FIG. 13A diagram showing a UV beams pattern irradiated out from a dish head uses in the germicidal station indicate with the dish head oscillating, the spaces are filed with UV beams, in accordance with an embodiment of the present disclosure.
Figure 13B:
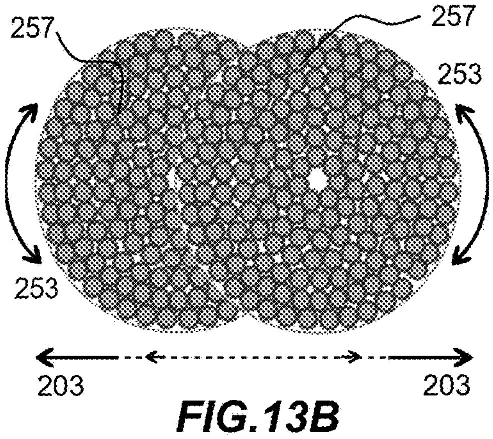
FIG. 13B diagram showing a UV beams pattern irradiated out from a dish head uses the germicidal station indicate with the dish head oscillating and the head started to sweep across in horizontal direction, the pattern becomes an elongated invisible painting covered with UV beams, in accordance with an embodiment of the present disclosure.

FIG. 1A is the multi-function cordless hand carrying high velocity high volume air blasting cannon 10 which is identical to the FIG. 1. An installed oscillating external foldable blades germicidal assembly 83 comprising an open center turntable 50 with inner ring 64 mounted on the exterior surface of germicidal chamber 30, the swivel outer ring 57 connects the foldable blades 46 via hinges 51, zoom and focusable UV LED 61 and UV Laser diode 47 are mounted on the face side of the blade 46, at the tip of blade 46 installed red 650 nm laser diode to guide the operator for visualize the target. In FIG. 1A the blades 46 are folded indicates the UV projectors 61, 47 are not deployed. Showing in FIG. 1B the external foldable blades germicidal assembly 83 is fully unfolded to deploy its UV projectors 47 or 61, because external foldable blades germicidal assembly 83 only has three blades 46 can produce three columns of UV beams 55 from the zoom and focusable LED 61, the invention uses beam scanning to fully fill the target being irradiating as shown in FIGS. 13,13A and 13B. This is done by oscillating motor 52 drives the turntable 50 causing the blades 46 oscillating in direction indicates on arrow 53 shown on FIG. 10 to effect irradiation pattern shown on FIG. 13B. This description is in accordance with an embodiment of the present disclosure.

Figure 2:
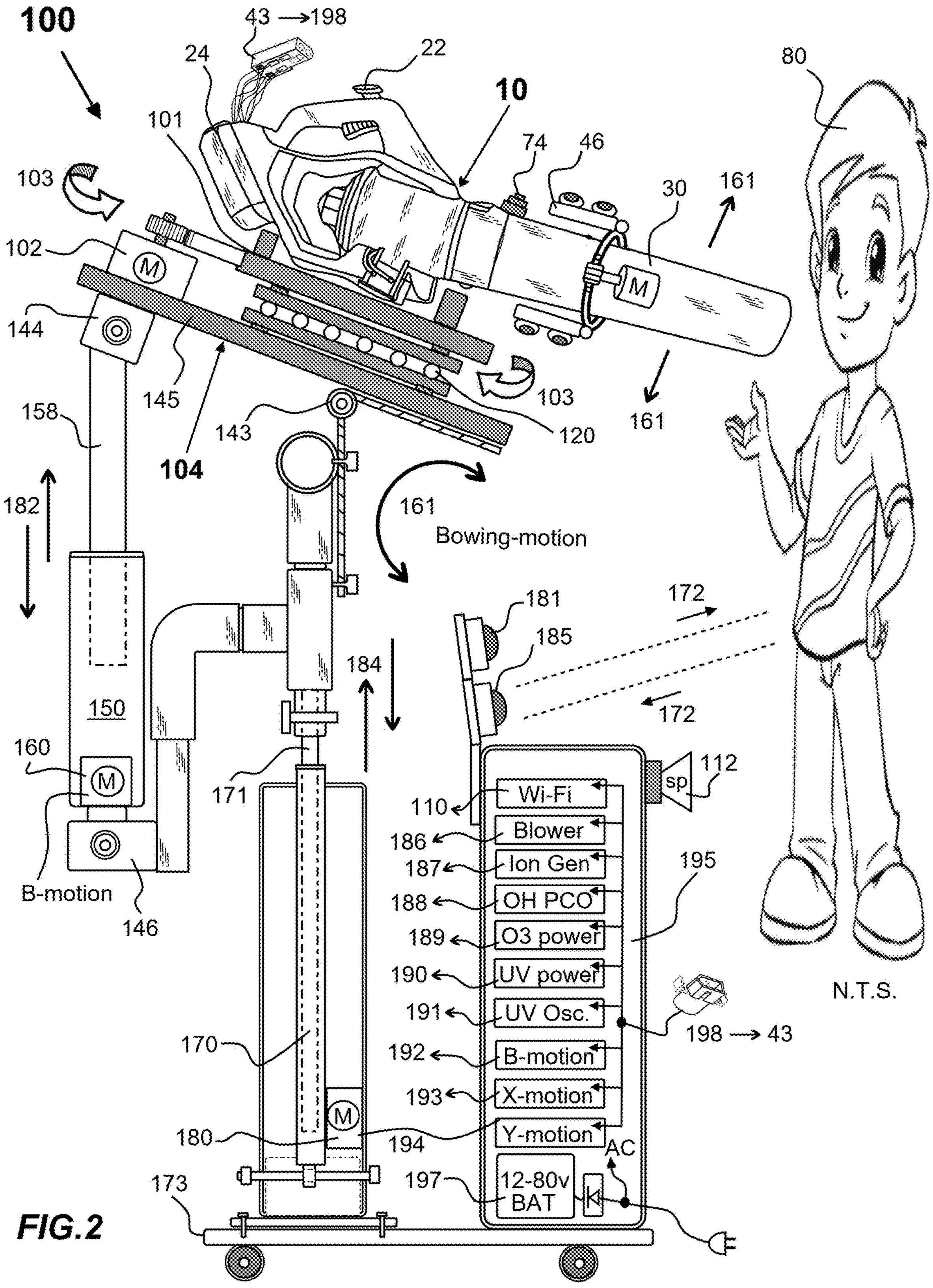
FIG. 2 is a plan perspective view of high velocity high volume air blasting cannon converted to an automated germs intercepting air blasting station to blast a person with ozone or hydroxyl showing the oscillating UV projectors mounted on the blades, the blades are in folded not in use position, in accordance with an embodiment of the present disclosure.

FIG. 2 is the multi-function cordless hand carrying high velocity high volume air blasting cannon 10 securely seated onto the wheeled floor stand 173 via a multi motion docking assembly 104 converting the cannon 10 to a hand free fully automated personal disinfection germs intercepting air blasting station 100. Station 100 comprising electronic system controller 195 houses a battery pack 197, elevation adjust Y-motion power supply 194, horizontal sweep x-motion 193 power supply, bow gesture B-motion 192 power supply, UV oscillating external foldable blades germicidal assembly 191 power supply, UV LED 190 power supply, ozone generator power supply 189, Hydroxyl generator power supply 188, bipolar ions generator power supply 187, fan power supply 186 and controller Wi-Fi power supply 110. Active or passive infrared sensor 185 take distance measurements via IR beam 172, if occupant 80 is present, the system 100 use twenty to forty seconds pre-programmed mode of operation such as selecting ozone module 34 blasting the occupant 80 with ozone 60 which is riding on high velocity air discharging from the cannon 10 nozzle 42. Particulates, pathogens 54 will be dislodged from the occupant's clothing and skin; pathogens 54 clinging on the occupant 80 will be inactivated. The blasting of ozone 60 takes about twenty seconds produce about 10.46×10^20 ozone molecules proactively seeking pathogens 54 to be inactivated. The germs intercepting air blasting station 100 comprising multi motion docking assembly 104 includes upper mount docking plate 101 attached to top side of turntable 120 and the lower mounting baseboard 145 attached to the bottom side of the turntable 120. AC synchronizes motor 102 drive the upper docking plate 101 causing the cannon 10 sweeping across horizontal plane direction indicates by arrow 103. A hinge 143 attached on bottom side of lower mounting baseboard 143 and bolted to elevation actuator assemblies include elevation motor 180, support tube 170, linear actuator push rod 171. Activate Y-motion power supply 194 will result lifting or lower the cannon indicate by arrow 184 for proper height to maximize the disinfecting of the occupant 80. A bow motion linear actuator 130 comprising motor 160, push rod 138, bottom bracket 146 attached to push rod 171 and top bracket 144 attached to lower mounting baseboard 143. Activate B-motion power supply 192 drive actuator rod 138 indicates by arrow 182 will result tilting the cannon 10 in bowing motion as indicated by arrow 161 blasting the occupant 80 from head to feet with ozone 60 or hydroxyl 70. A power socket 108 mates with power plug 43 provide power to cannon 10 to bypass its battery 24. Camera 181 detects occupant present and play prerecorded warning announcement via speaker 112 to vacant the area when UV projectors 47, 61. This description is in accordance with an embodiment of the present disclosure.

Figure 3:
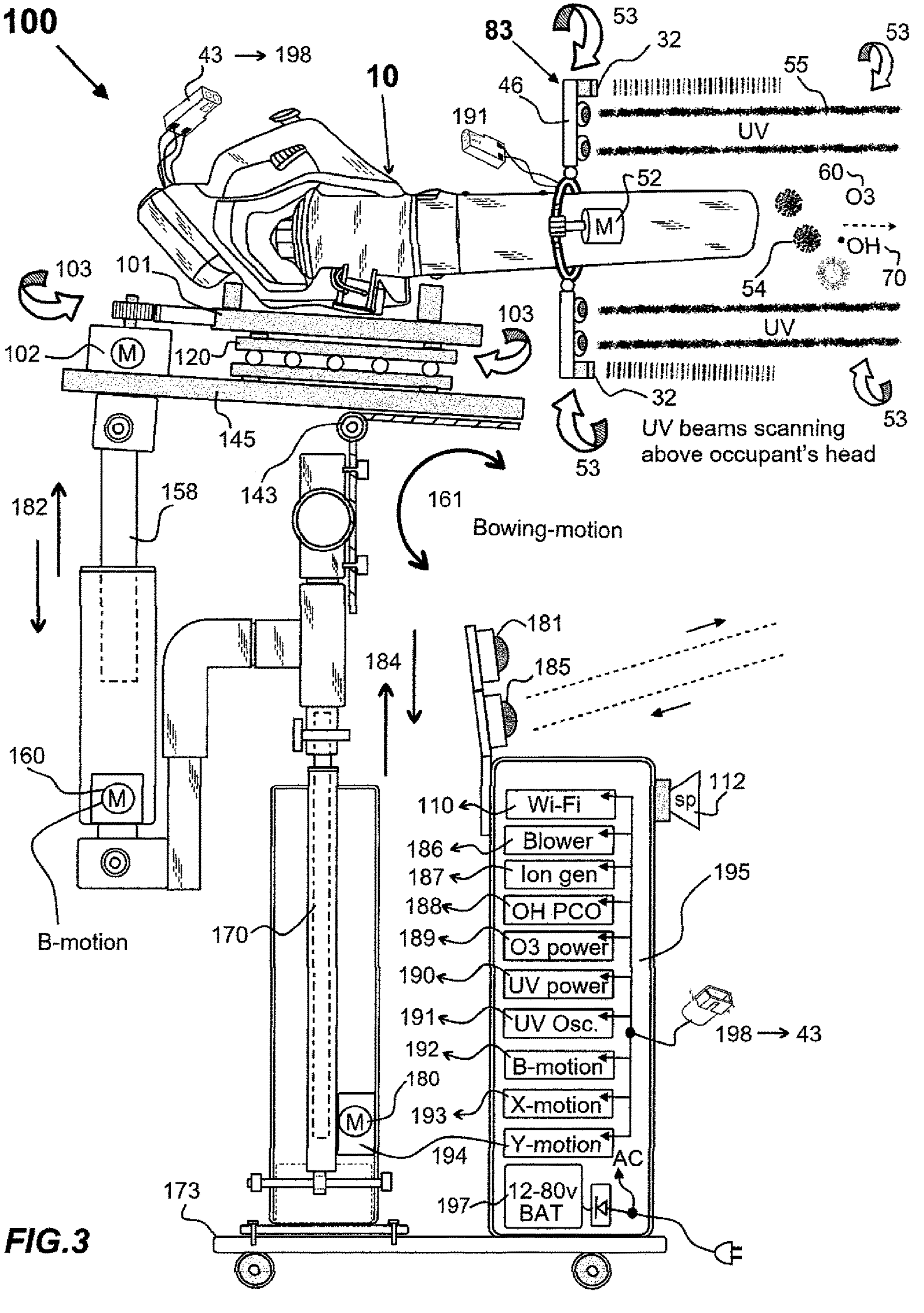
FIG. 3 is a plan perspective view of high velocity high volume air blasting cannon converted to an automated germs intercepting air blasting station to effect upper room germicidal function showing the oscillating UV projectors and parametric ultrasound speakers are mounted on the blades are fully unfolded for UV beams, parametric ultrasound speakers and air blasting pathogens inactivation, in accordance with an embodiment of the present disclosure.

FIG. 3 is identical to FIG. 2 with the oscillating external foldable blades germicidal assembly 83 deployed. The activated UV irradiant 33 should not be used if occupant 80 present. For illustration purposes only zoom and focusable UV LED 61 is selected. UV Laser diode 47 projects very narrow beam when focused is great for long range irradiation. For a small room, the focusing lens is removed; causing the built-in collimated coherent beam of laser diode 47 produces wide spread irradiation is ideal for a small room non-human occupied application. If the germicidal station 100 intended uses as an upper-room germicidal application, set the elevation to above occupant's head level, and use only the focused beams settings on the LED 61 or laser diode 47 or combination of both to avoid fringe irradiant shifted below occupant's head. The parametric ultrasound speakers 32 are shown mounted on the blades 46. If speaker 32 is selected, the ultrasound speakers 32 blasting modulated ultrasound energy to destroy pathogens 54 on air. This description is in accordance with an embodiment of the present disclosure.

Figure 4:
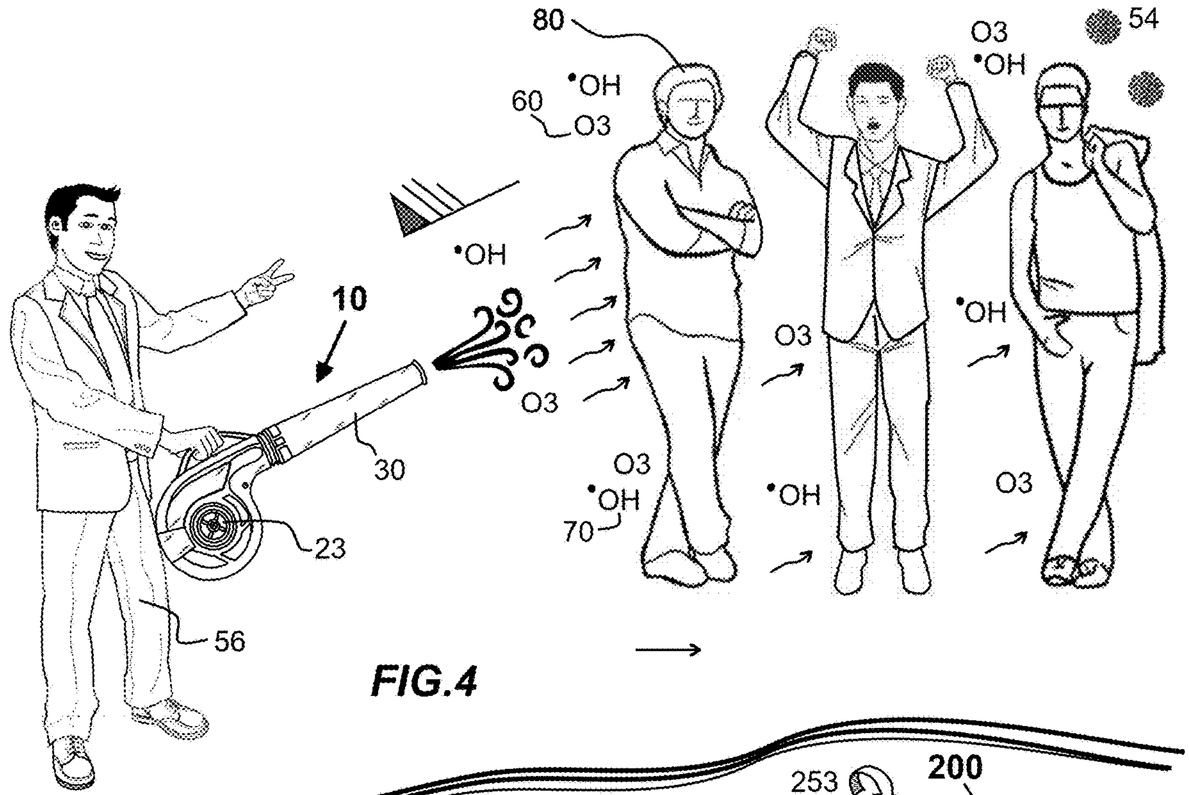
FIG. 4 is a perspective view of a multi-function battery operated cordless hand carrying high velocity high volume air blasting cannon showing a group of people being blasting with air for germicidal disinfection, in accordance with an embodiment of the present disclosure.

An application example of germicidal cannon 10 is shown on to FIG. 4 user 56 blasting hydroxyl 70 or ozone 60 to disinfect a group of occupants. Ozone 60 or hydroxyl 70 riding on air exiting from cannon 10 speeds up to 110 MPH at 600 CFM high velocity air blasting the occupants, the accelerated ozone 60 or hydroxyl 70 dislodge particulates and inactivating pathogens 54 from their skins and clothing. Accelerated high impact hydroxyl 70 or ozone 60 deeply imbedded into weaving lines between fabrics materials efficiently inactivates pathogens 54 that clung to occupants. Ozone 60 can remains in the clothing for about fifteen minutes has ample time to inactivate stubborn pathogens 54.

Figure 5:
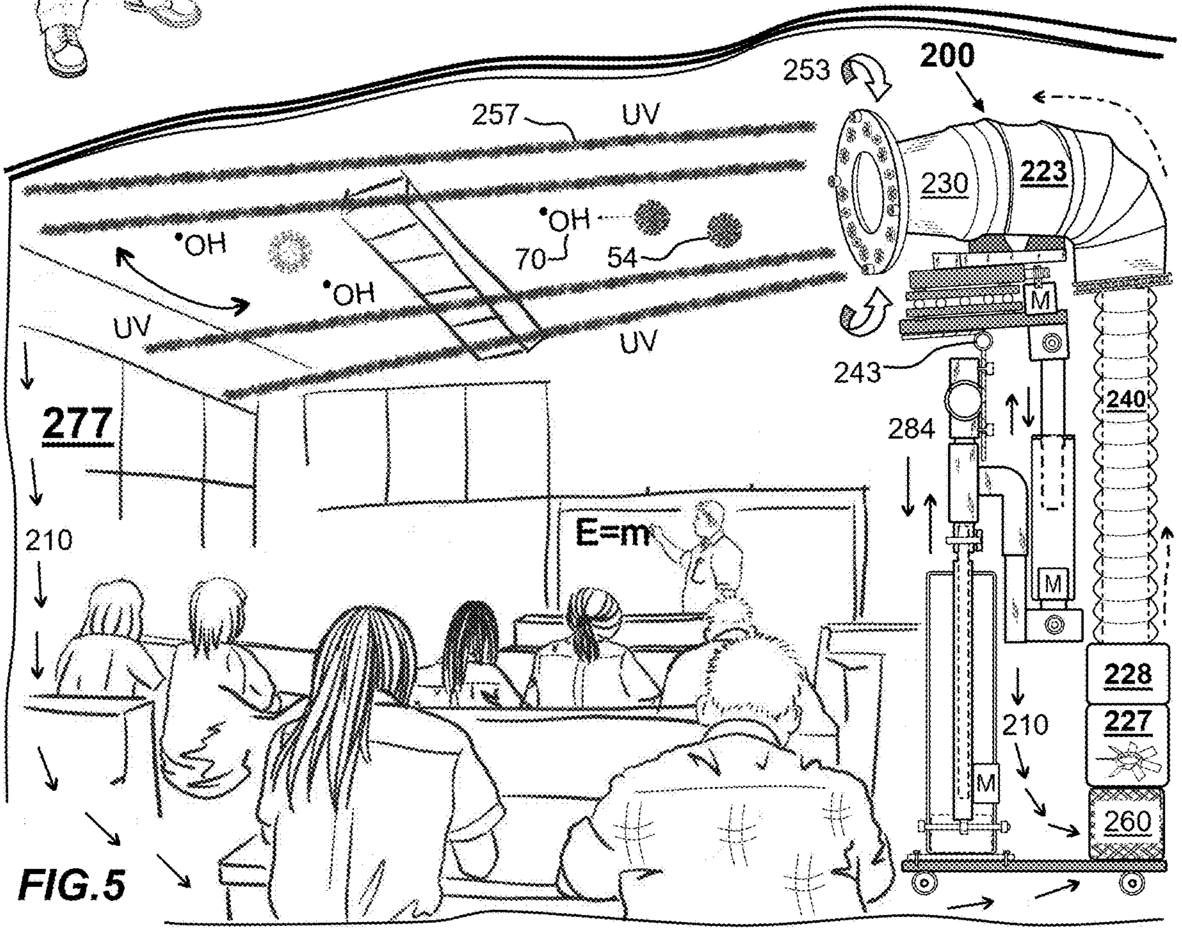
FIG. 5 is a perspective view of a multi-function germicidal station performs upper room germicidal is placed inside a classroom for continuous operation with occupants present, in accordance with an embodiment of the present disclosure.

FIG. 5 is an upper-room multi-function germicidal station 200 placed in a small classroom 277. Their focused LED UV beams 257 sweeping across horizontal plane reaching the other side of wall. Pathogens 54 will be inactivated along the path of focused beams. This description is in accordance with an embodiment of the present disclosure.

Figure 6:
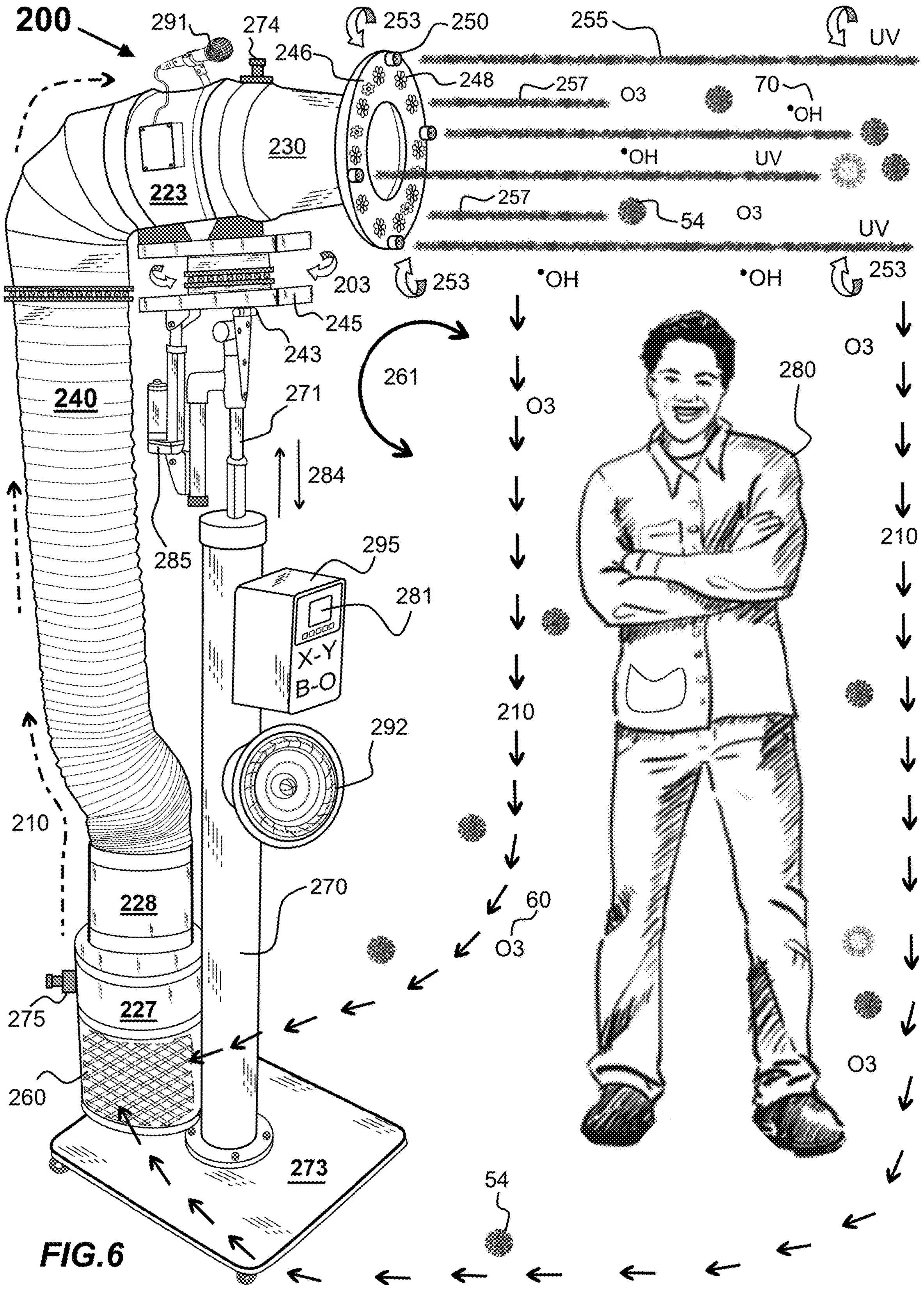
FIG. 6 is a perspective view of a multi-function germicidal station placed inside a structure for upper room continuous operation with occupants present. Showing the UV beams are always above a person's head level, its forced air travels in long range then picks up from lower floor level fan for repeating pathogens inactivation. An active noise cancellation control circuit to reduce the noises of high volume fans, in accordance with an embodiment of the present disclosure.

FIG. 6 is identical to FIG. 5 showing an occupant 280 safely stands below the irradiating focused beams 257. The station 200 performing the user selected module may include ozone 234, hydroxyl radical generator combination module 294 include titanium dioxide 235 coated plates 236, 237 with multi wavelength UV light source 238, or bipolar ions emitters 233, 239. This description is in accordance with an embodiment of the present disclosure.

Use of ozone module 234 should only be in an unoccupied room because excessive exposure to ozone molecules 60 may harm occupant's respiratory system.

Figure 7:
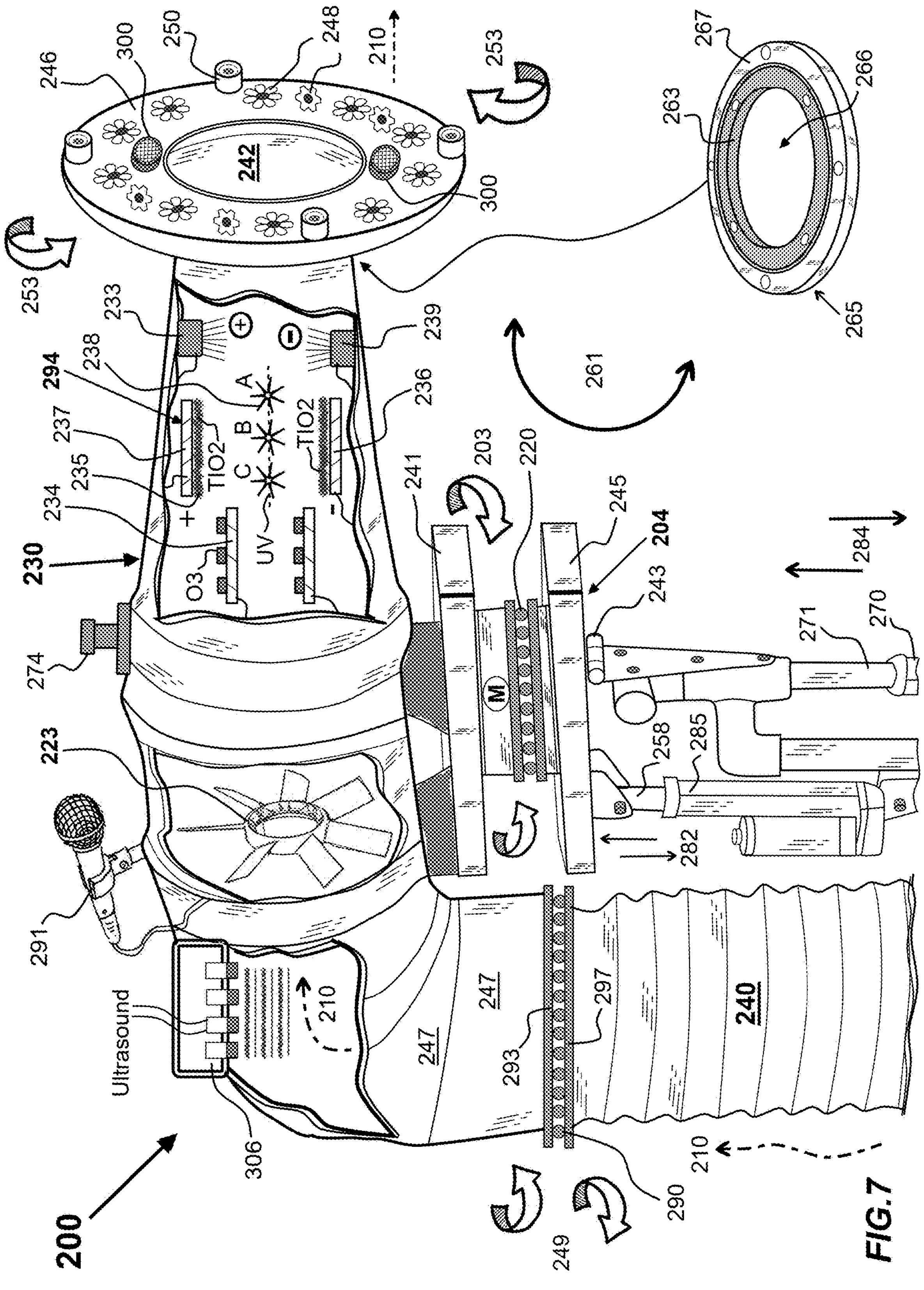
FIG. 7 is a plan perspective view of a multi-function germicidal station showing the exposed interior modules inside the internal germicidal chamber and water vapor inlet, in accordance with an embodiment of the present disclosure.

An alternative to the invention 200 is switching to activate the germicidal chamber 230 with harmless hydroxyl radicals generator combination module 294 shown on FIG. 7. The module comprising multi wavelength UV light source irradiators 238 shinning the light sensitive TIO2 semiconductor coating 235 on the surface of charge plates 237, 236 to effect photocatalysis conversion to generate hydroxyl radicals 70 blasting out through germicidal nozzle 242. Once exited, the hydroxyls 70 riding on about 35 MPH wind front the fan 223 continuing on its journey at 51 feet per second speed. If the room is less than 51 feet wide, the hydroxyls 70 are forced to move downward due to air convection effect. In a larger room, the hydroxyls 70 eventually disperse and move toward to lower floor level. The dispersing hydroxyls 70 inactivate pathogens 54 on their path then picked up from the lower floor fan 227 and particulates filter 260 via a flexible air duct 240 in series with an elbow 247 back to fan 223 for repeating pathogens 54 inactivation as shown by arrow 210. Injecting vaporized water via inlet 274 will increase hydroxyl radical 70 outputs. FIG. 7 further indicates a parametric ultrasound speaker array 306 imbedded inside the air delivery elbow 247. When the speakers 306 activated, the ultrasound wave from speaker array 306 traveling against the headwind 210 will be refracted to all sides of the inner surface of duct 240 causing pathogens 54 to spin and oscillate to further weakening and damaged the pathogens 54. Because the germicidal chamber 230 moves in sweeping motion indicates by arrow 203 on FIG. 7 and FIG. 15. The air delivery elbow 247 connected to flexible air duct 240 must be oppositely sweeping in synchronises with the elbow 247. The invention disclosed a large diameter open center 296 anti-stalled open center turntable 290 with its inner ring 293 connected to elbow 247 and its outer ring 297 connected to the flexible air duct 240 to prevent stalling the movement of the sweeping motion 203. Another alternative to provide nozzle 242 in sweeping motion is to install an oscillating motor between the vertical motion linear actuator 270 and the stationary wheeled stand 273 to cause the entire station 200 in oscillation motion. This description is in accordance with an embodiment of the present disclosure.

For a dusty room, a user can select bipolar ions module 233, 239 showering the room for a pre-filtering of the room. The negative ions 58 attract positively charged particulates and positive ions 59 attracting negatively charged particulates causing them to be too heavy to stay airborne and quickly particulate to the floor for dust collection and disposal.

The methods of using ozone module 234 to inactivate pathogens 54 and bipolar ions module 233, 239 are the same procedures as described in operation of the hydroxyl module 294 above.

Returning to FIG. 6 the station 200 comprising a motorized or wheeled floor-stand 273, an elevation actuator 270 with its push rod 271 supporting a hinge 243 and a bow motion actuator 285. The station 200 further comprising a multi motion docking assembly 204, the underside of lower mounting baseboard 245 connected to the hinge 243 and the upper bracket of push rod 258, a motorize turntable 220 sandwiched between the top side of lower mounting baseboard 245 and oscillating motion upper mount docking plate 241. Upper plate 241 securely bolted to the fan motor housing 223 that connected to elbow 247 and the germicidal chamber 230 and the dish head 246 shown on FIG. 7. Activate the actuator 270 will move the motor housing 223 in up and down direction shown on arrow 284, activate the actuator 283 in direction arrow 282 will cause the motor housing 223 in bowing gesture motion indicates by arrow 261. An open center 266 turntable 263 with its inner ring 263 bolted onto the outer surface of chamber 230 and the outer ring 267 attached to the dish head 246. An AC synchronize motor 232 attached on the outside surface of chamber 230 driving the dish head 246 via a drive arm 268 in oscillating motion indicated by arrow 233 shown in FIG. 8B, FIG. 15. This description is in accordance with an embodiment of the present disclosure.

As mentioned earlier, the flexible air duct 240 also needs to sweep in the opposition direction in reference to the sweeping direction of the dish head 246. An open center 296 turntable 290 inner ring 293 connecting the elbow 247 and outer ring 297 connecting to the flexible air duct 240, when the elbow 247 swinging in direction 249 as shown in FIG. 7 only causing the turntable 290 rotates to avoid stalling the multi motion assemblies 204. This description is in accordance with an embodiment of the present disclosure.

Noise control is important when the high volume fan 223 is set to highest power output inside an occupied room. A microphone 291 listening to the fan's produced white noises, and then feeds to a popular anti fan noise circuitry; Active Noise Control AD73522 DSP Converter available from Analog Devices Inc, implemented as reserved to the disclosure, present and further developed. Shown in FIG. 6 is the anti-noise speaker 292 for phases cancelling the fan noises. This description is in accordance with an embodiment of the present disclosure.

Figure 14:
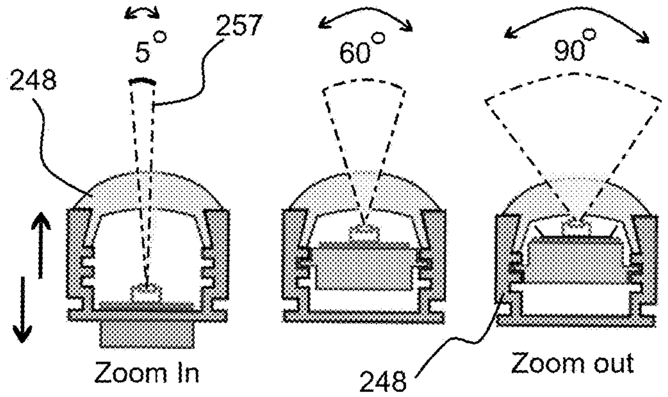
FIG. 14 diagram showing how zoom and focusable LED light works, in accordance with an embodiment of the present disclosure.
Figure 14A:
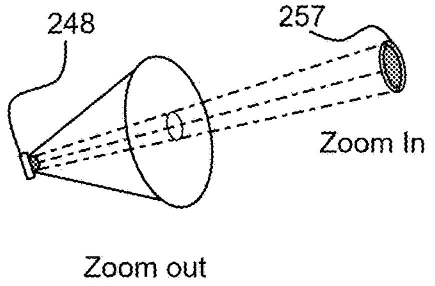
FIG. 14A diagram showing a perspective drawing of a zoom and focusable LED light, in accordance with an embodiment of the present disclosure.

The station 200 further comprising external pathogens 54 inactivation dish head 246 shown on FIG. 7,8,8B mounted with arranged pattern of multi wavelength UV LED 248 or UV laser diodes 250 for pathogens 54 inactivation and red 650 nm or other color laser diodes for visually guiding the user where are the invisible UV beams 257 are irradiating. The UV LED 248 zoom and focusable to very intense narrow beams that pathogens irradiated with the beams 257 will be quickly inactivated as illustrated in FIG. 14,14A. The laser diodes 250 are already collimated and coherence is great for small room disinfection, a simple fused glass lens is placed in front of the laser diode to focus the beams for long range disinfection application. FIG. 8A is comparing the beams size of the zoom and focused LED 257 and focused laser diode 255 and the red laser 244 for visual guiding purposes. This description is in accordance with an embodiment of the present disclosure.

Figure 8:
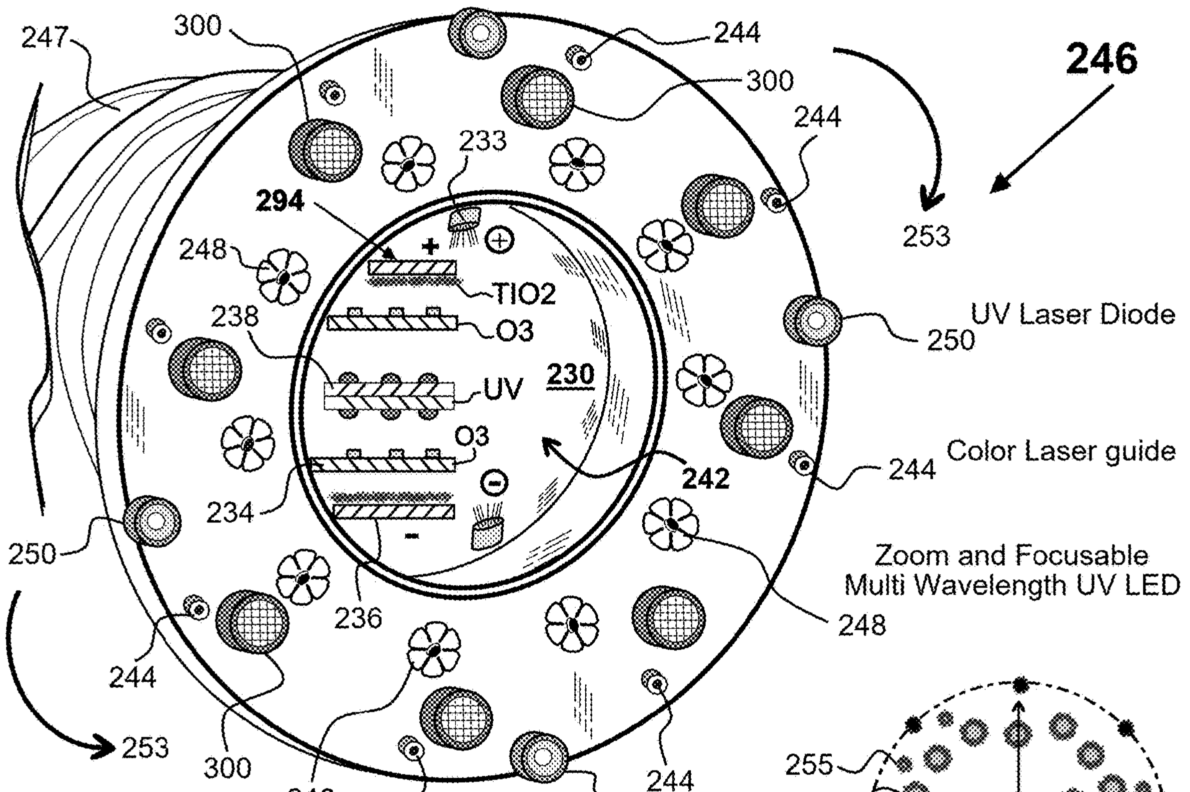
FIG. 8 is a front perspective view of a multi-function germicidal station showing external dish head conical nozzle germicidal assembly mounted with zoom and focusable UV LED, array of parametric ultrasound speakers and UV laser diodes, also a group of red 650 nm laser diodes for guide the user intended target area location, in accordance with an embodiment of the present disclosure.
Figure 8A:
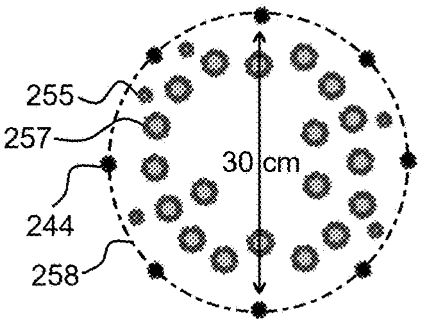
FIG. 8A is a diagram representing the projected beams pattern. Showing larger beams are focused UV LED, smaller beams are UV laser. Darker beams are red laser for indication where are the beams located, in accordance with an embodiment of the present disclosure.
Figure 8C:
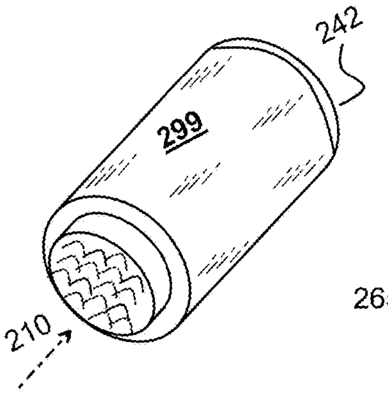
FIG. 8C is a muffler lined with egg crate shaped foam attaches in front of air discharge conical nozzle to reduce wind noises, in accordance with an embodiment of the present disclosure.

FIG. 8 shows an array of parametric ultrasound speakers 300 mounted on the dish head 246 provides greater alternative to UV lights 250, 248 in some situation. This description is in accordance with an embodiment of the present disclosure.

Figure 8B:
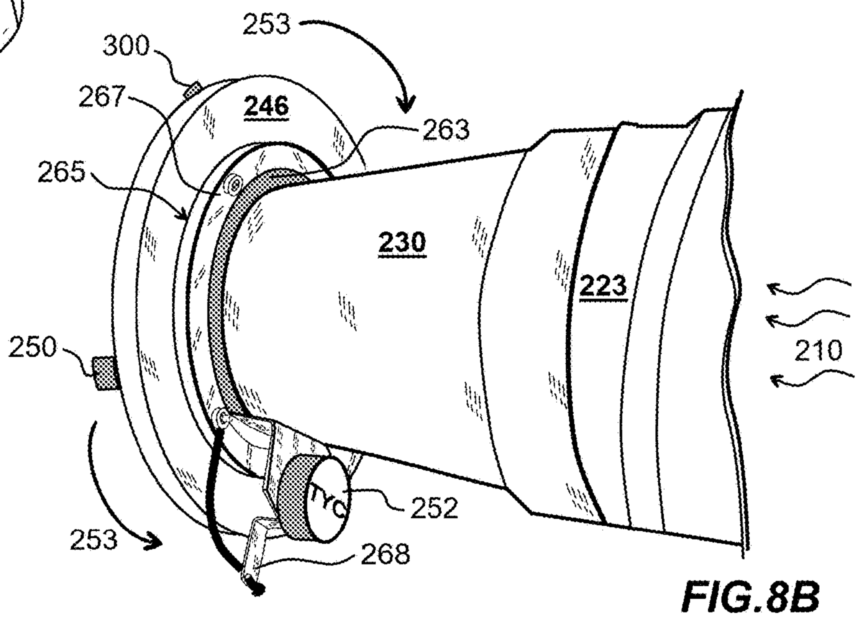
FIG. 8B is rear side of a plan perspective view of external dish head conical nozzle germicidal assembly showing rear side of dish head mounted on an open center turntable, an AC synchronize motor drive the turntable to cause the dish oscillate, in accordance with an embodiment of the present disclosure.
Figure 15:
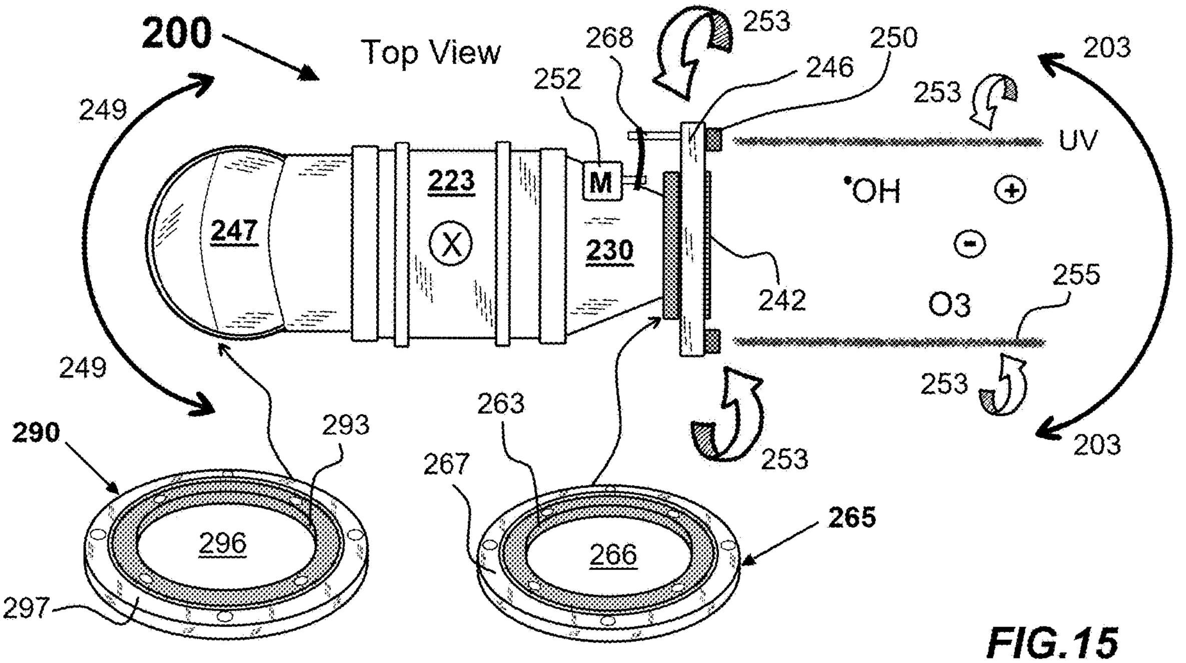
FIG. 15 is top view of a multi-function germicidal station showing an air delivery elbow, a fan, germicidal chamber, an open center turntable connecting the chamber and dish head, another open center turntable connecting the air delivery elbow and the flexible air duct below, in accordance with an embodiment of the present disclosure.

The dish head 246 has a center opening 242, there is always some spots in the germicidal chamber nozzle 242 not fully covered with UV beams 257, the invention shown in FIG. 8B equipped with an AC synchronize motor 252 and linked to an arm 268 driving the dish head 246 in oscillating motion as shown by arrow 253 as illustrated in FIG. 13 beams pattern of placement of UV projectors 248, FIG. 13A is the beams 257 pattern in oscillating motion, FIG. 13B with dish head 246 oscillating and the multi motion docking assembly 204 in sweeping motion shown in FIG. 15 by arrow 203 result in a fully UV beams 257 covered, the width of dish head 246 rectangular shaped beams 257. This description is in accordance with an embodiment of the present disclosure.

Figure 6B:
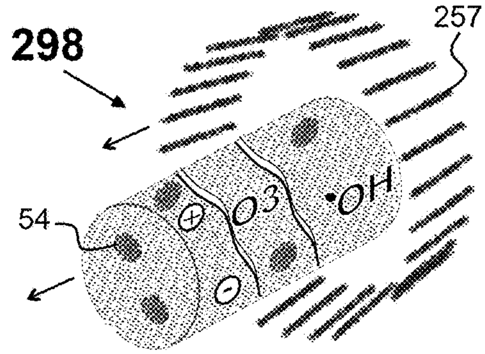
FIG. 6B is a front perspective view of a virtual beam cage formed by the UV beams of the oscillating dish head, showing exiting pathogens being encircling with UV beams in the form of co-extrusion fashion, in accordance with an embodiment of the present disclosure.
Figure 6A:
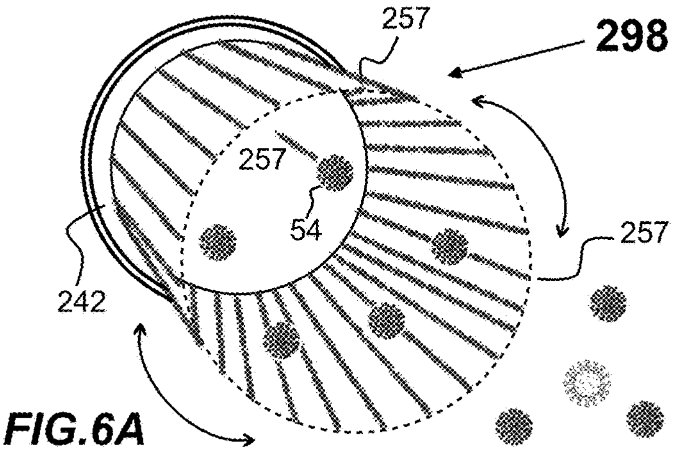
FIG. 6A is a front perspective view of a virtual beam cage formed by the UV beams of the oscillating dish head, showing pathogens being encircling with UV beams, in accordance with an embodiment of the present disclosure.

The projecting beams 257 from the dish head 246 configured to forming a virtual UV beam cage 298 depicts in FIG. 6A. The exiting pathogens 54 that missed the internal germicidal chamber 230 traveling alongside with the UV beams 257 are in a co-extrusion fashion shown in FIG. 6B encircling by the beams 257. As the dish 246 sweeps in direction indicated by arrow 203, pathogens 54 will be inactivated by the encircling beams 257. Pathogens 54 within the upper room region will also be quickly inactivated. This description is in accordance with an embodiment of the present disclosure.

Figure 9:
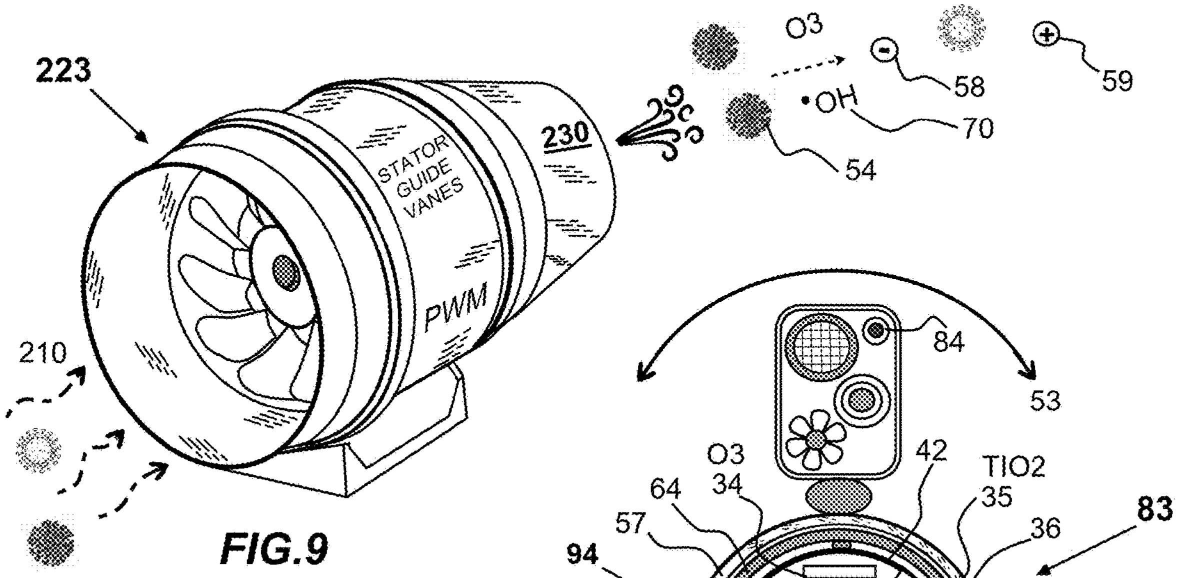
FIG. 9 is a front perspective view of a multi-function germicidal station showing the inline fan moves contaminated air into the germicidal chamber, out with ozone, hydroxyl, and negative ions and escaped pathogens, in accordance with an embodiment of the present disclosure.

Turning to FIG. 9 is a Pulse Width Modulated inline fan 223 with installed stator guide vanes to direct the exiting air travel farther with reduced wind noises, shown here are pathogens 54 pulls in from lower floor level due to convection, contaminated air pass through internal germicidal chamber 230 discharging at the nozzle 242 still remaining some remnant pathogens 54. This description is in accordance with an embodiment of the present disclosure.

Turning to FIG. **1*l* is using germicidal cannon 10 to disinfect occupant 80 at indoor, such as inside an airport, the dislodged particulates and pathogens 54 collect at the rear booth for disposal on behind the occupant 80** being blasted. This description is in accordance with an embodiment of the present disclosure.

Figure 12:
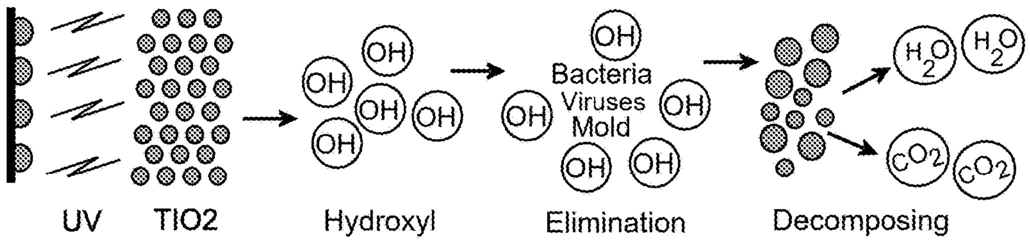
FIG. 12 a diagram shows how indoor photocatalysis works, in accordance with an embodiment of the present disclosure.

FIG. 12 is the basic principle how hydroxyl radical 70 is created at in indoor environment through UV light and TIO2 semiconductor. This description is in accordance with an embodiment of the present disclosure.

Figure 16:
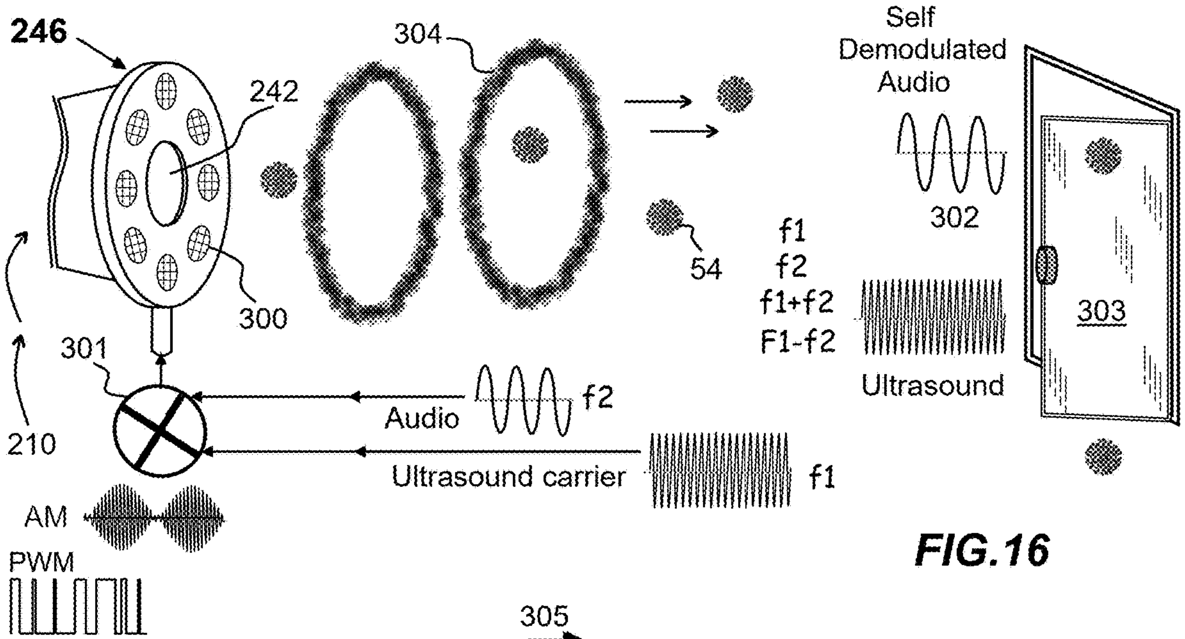
FIG. 16 diagram showing using parametric ultrasound speakers arrange in an array producing rings of audio modulated ultrasound directional beam to destroy pathogens in air, in accordance with an embodiment of the present disclosure.

FIG. 16 is an illustration of parametric ultrasound speaker 300 mounted on oscillating dish head 246 configures a highly directional focused beam propagating toward a door 303. An ultrasound carrier F1 is 26 kHz modulating with audio F2 is 500 Hz at mixer circuit 301. Each speaker 300 has a speaker diaphragm having diameter 0.5 inch (12.7 mm) to best match the frequency of air impedance. Each speaker 300 wave front will combine naturally in air forming large planar wave 304 propagating straight to the door 303 without suffers inverse-square-law and retains minimum dispersion. The high energy 26 kHz planar wave 304 damages the pathogen 54 in air and those exiting the ring shaped wave 304. When the wave 304 encountering solid object, such as door 303, the audio 302 break loose becomes self-demodulated audio by heterodyne process in air. The self-demodulated audio 302 creates 500 Hz mechanical vibrations dislodging pathogen 54 from clinging on door 303. The fallen pathogen 54 then suck up by fan 227 through forced air convection. The 500 Hz tone is audible only when someone facing directly at the door 303 but it is annoying to unintended listener. A white noise audio F2 can be substituted if it is a concern. This description is in accordance with an embodiment of the present disclosure.

Figure 16A:
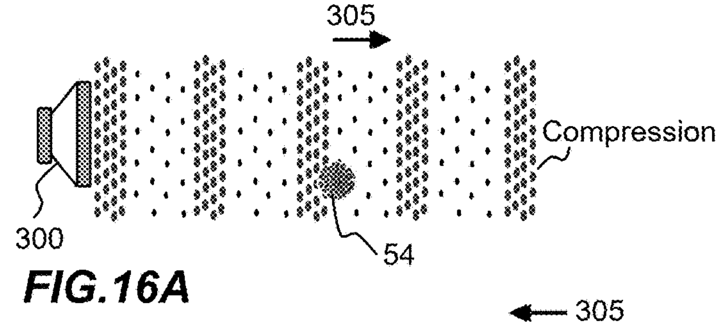
FIG. 16A graphic illustrates pathogen traps in the ultrasound active zone, the pathogen being pushed to right during compression phase, in accordance with an embodiment of the present disclosure.
Figure 16B:
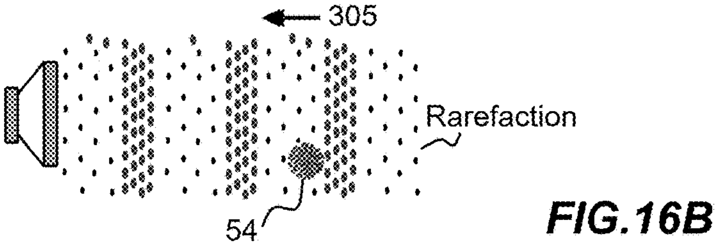
FIG. 16B graphic illustrates pathogen traps in the ultrasound active zone, the pathogen being pulled to left during rarefaction phase, in accordance with an embodiment of the present disclosure.

FIG. 16A illustrating how ultrasound destroy pathogen. As the source 300 expands it pushes the surrounding air molecules away causing them to bunch together and the air pressure to increase. This is called compression. Pathogen 54 being pushed to right as indicates by arrow 305. FIG. 16B As the source 300 contracts the surrounding air molecules spreads out to fill the increasing space, causing a decrease in air pressure. This is called rarefaction. Pathogen 54 moving back to left as indicates by arrow 305. Each individual air molecules and pathogen 54 do not travel from the source 300 to the door 303, but oscillate or vibrate back and forth twenty-six thousand times per second around a fixed point can cause ultrasonic cavitation and damaging the pathogen 54 to perform its function. This description is in accordance with an embodiment of the present disclosure.

Figure 17:
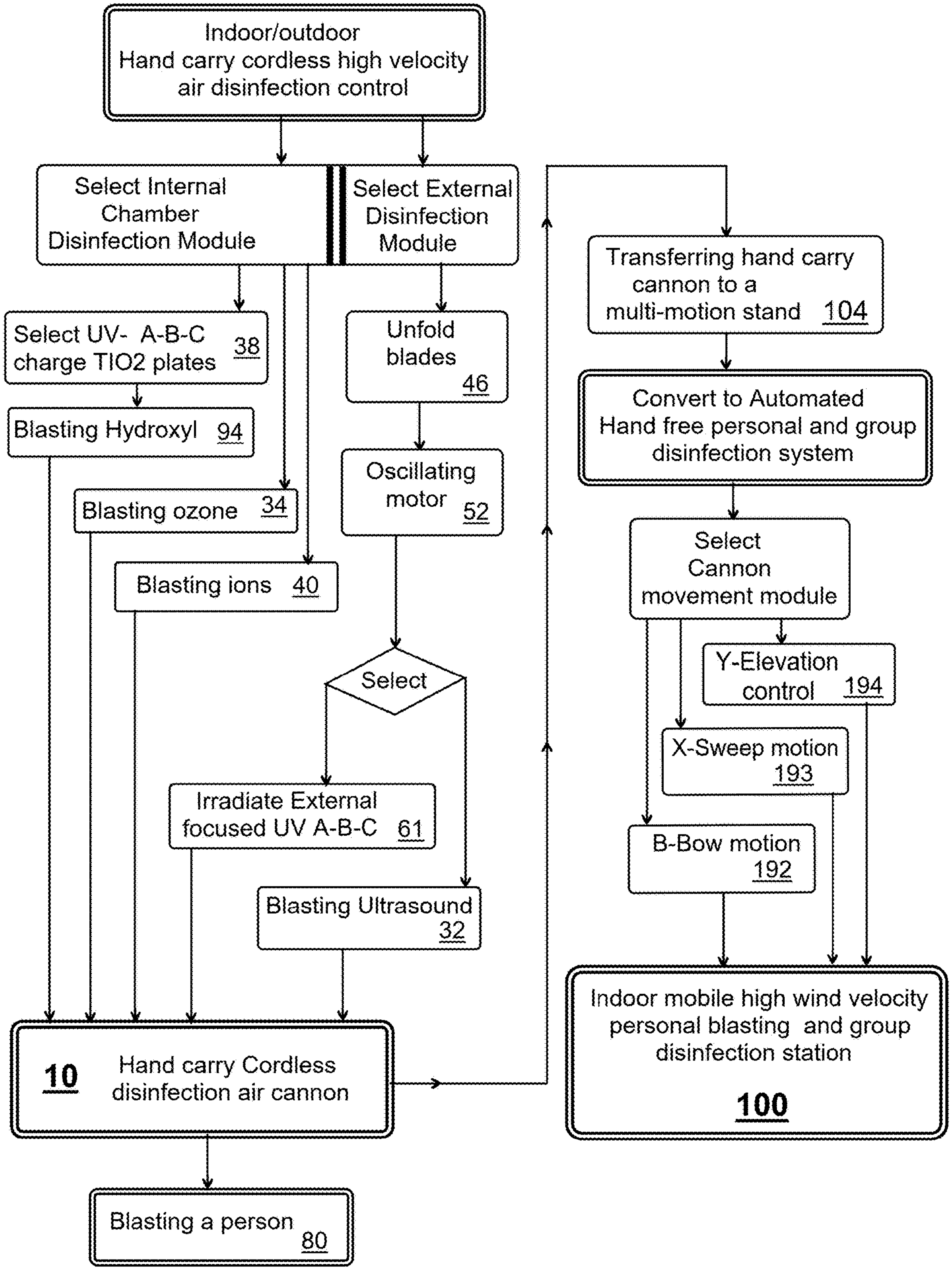
FIG. 17 diagram showing operation of a multi-function battery operated cordless hand carrying high velocity high volume air blasting cannon and converted to germs intercepting air blasting station, in accordance with an embodiment of the present disclosure.

A flow diagram in FIG. 17 illustrates the hand carry cordless germicidal high velocity high volume air blasting cannon 10 for use disinfect a person by blasting high velocity air mixing with ozone 60 or hydroxyl 70, with adding a floor stand 173 shown on FIG. 2 easily converts to hand free germs intercepting air blasting station 100. This description is in accordance with an embodiment of the present disclosure.

Figure 18:
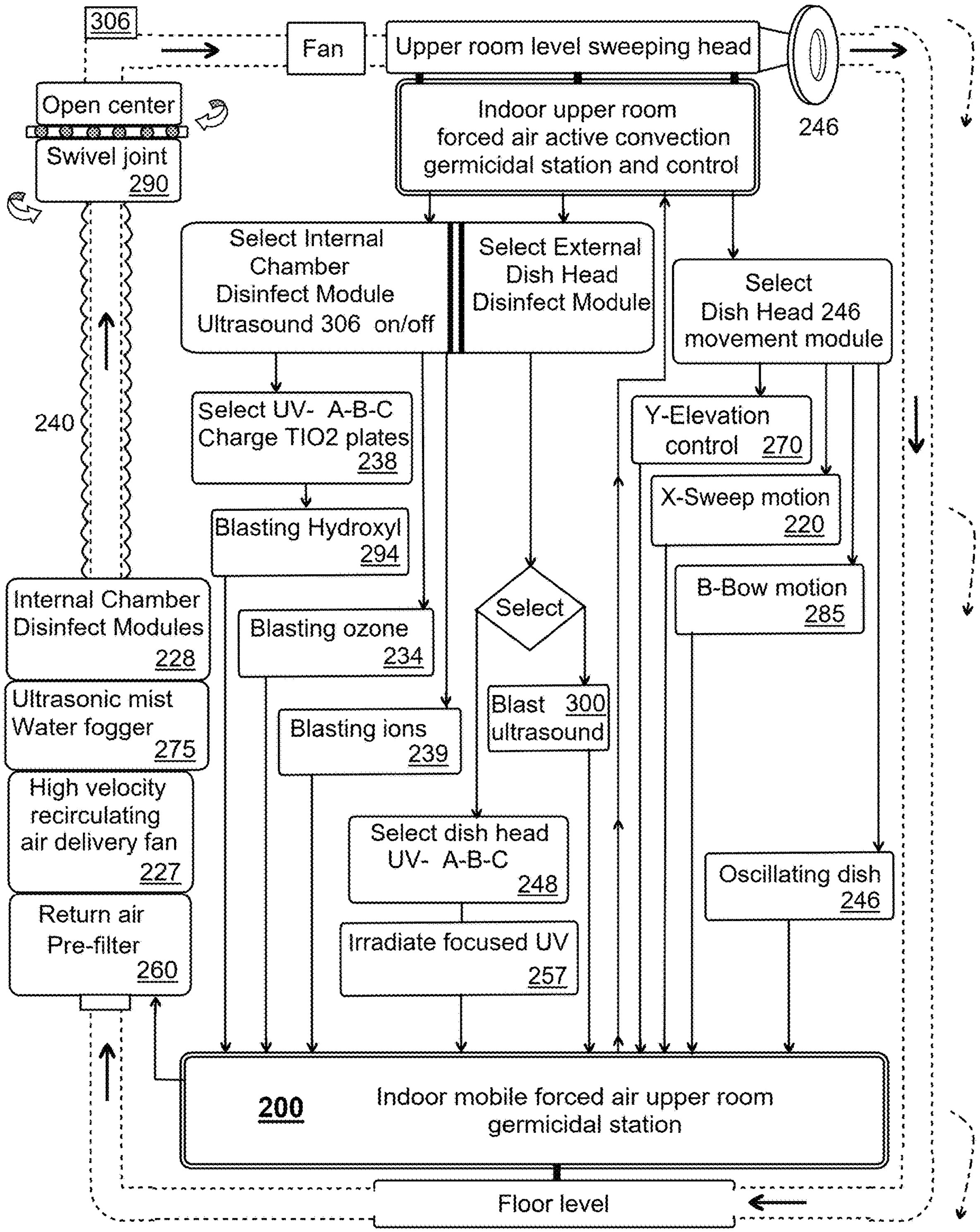
FIG. 18 diagram showing operation of a multi-function germicidal station with active air convection, in accordance with an embodiment of the present disclosure.

Another flow diagram in FIG. 18 illustrates an occupant safe, upper room germicidal station 200 features active convection re-circulate air from the source to far-end, that is from lower floor level to ceiling level utilizing air sweeping nozzle 242 in synchronize with opposite sweeping return flexible air duct 240, selectable multi modules include ozone 234, hydroxyl assemblies 294, bipolar ions 233, 239 for pathogens 54 disinfection, a virtual UV beam cage 298 created by projected intense focused UV beams 257 and an array of parametric ultrasound speakers 300 encircling untreated pathogens 54 left from internal germicidal chamber 230 as well as pathogens 54 in the upper room region. This description is in accordance with an embodiment of the present disclosure.

The germicidal station 200 connects to its wireless modem to communicate from remote location, this feature allows ozone 234 module to be activated and monitors via its camera 281 for emergency shut down when occupant present. This description is in accordance with an embodiment of the present disclosure.

In general, surface disinfection of one log reduction requires UV dosage for a 90% kill of most bacteria and viruses range from 2000 to 8000 micro watt times second per square centimeter at one meter distance from UV source. The weak UV intensity offered by the conventional tube lamp, such as Mercury arc lamp germicidal devices on the market drops off follows by the inverse-square-law. The invention retains its intensity much less affected by the distant; it is an advantage of zoom and focusable UV LED 248 and the directional focused parametric ultrasound speakers 300. When the Minamata Convention becomes soon implemented, the use of conventional low pressure mercury UV lamps will be prohibited. This description is in accordance with an embodiment of the present disclosure.

In upper room germicidal, ideally all upper room measurements should be around 30 $\mu W/cm^2$ to 50 $\mu W/cm^2$ at 10 feet from the fixture. The invention offers 3 logs 99.9% reduction using the zoom and focusable multi wavelength UV LED projector 248 adjusted beam diameter to half inch (12.7 mm) at feet (6 meter) at about 10 milliwatt 275 nm has enough energy to inactivate pathogens 54 quickly upon irradiated. This description is in accordance with an embodiment of the present disclosure.

Although the operations of the method(s) herein are shown and described in a particular order, the order of the operations of each method may be altered so that certain operations may be performed in an inverse order or so that certain operations may be performed, at least in part, concurrently with other operations. In another embodiment, instructions or sub-operations of distinct operations may be implemented in an intermittent and/or alternating manner.

What is claimed is:

1. A multi-function germicidal station comprising:

an active noise cancellation circuitry paired with a microphone and an audio speaker configured to reduce an air blower fan noise;

a vertical motion linear actuator supported by a wheeled pole floor stand, and an electronic system controller;

a bow motion linear actuator supported by a multi motion docking assembly;

a first end of an air delivery elbow connected to a ceiling level internal germicidal chamber further connected to a germicidal assembly;

an oscillation motion open center turntable encircling over a conical nozzle of an external dish head conical part of the germicidal assembly;

an anti-stalled open center turntable jointing a second end of the air delivery elbow and flexible air duct clamped onto a floor level internal germicidal chamber; and a high volume air blower fan moving air from a floor level intake air filter through at least one internal germicidal chamber through the anti-stalled open center turntable via the external dish head conical nozzle germicidal assembly (EDHCNGA) supported by the multi motion docking assembly, wherein the bow motion linear actuator directs an exiting high volume of air in three dimension directions of active forced air convection.

2. The multi-function germicidal station of claim 1, wherein the multi motion docking assembly is driven by a horizontal sweeping motion motor (HSMM) comprising a stationary lower mounting baseboard attached to a top section of a hinge and an oscillating motion upper mount docking plate securely holds the ceiling level air delivery elbow and EDHCNGA, wherein activating the HSMM turns the air delivery elbow and EDHCNGA discharging air oscillating in an horizontal sweeping motion.

3. The multi-function germicidal station of claim 1, wherein, a bottom section of hinge attached to an extendable and a retractable supporting rod of the vertical motion linear actuator and a stationary portion of a housing of the vertical motion linear actuator is bolted to the pole floor stand, activates the vertical motion linear actuator to raise or lower the air delivery elbow and EDHCNGA for elevation adjustment.

4. The multi-function germicidal station of claim 1, wherein a bottom section of a hinge jointly connected to a stationary portion of a housing of the bow motion linear actuator includes an extendable and retractable supporting rod of the bow motion linear actuator pivotal mounted away from the hinge's center axes onto a lower mounting baseboard of the multi motion docking assembly, wherein a relative pivot distance defines an area for treatment, activates the bow motion linear actuator and causes the multi motion docking assembly to rotate between a clockwise and a counter clockwise direction as observed on a side.

5. The multi-function germicidal station of claim 1, wherein the ceiling level internal germicidal chamber comprises a high volume air blower fan, an ozone generator module, a hydroxyl generator module, a bipolar ions generator module, a multi wavelength ultraviolet light source module and switching electrostatic charge plates coated with a Titanium Dioxide semiconductor material module effecting photocatalytic oxidation (PCO), wherein the placement of the ceiling level internal germicidal chamber relocated to floor level becomes a floor level internal germicidal chamber.

6. The multi-function germicidal station of claim 1, further comprising a surface mounted EDHCNGA comprising a group of multi wavelength zoom and focusable UV LED (ultra violet light emit diodes) and laser UV diodes, having a wavelength from 200 nm to 400 nm and distributed throughout the dish head by adjusting their focal point intensity and their light dispersion by a collimator and optical lens for fast pathogen disinfection and a motor driven oscillation motion open center turntable attached to the EDHCNGA in oscillation motion reduces pixilation gaps due to a low spreading focused group of UV beams of 650 nm red laser diodes mounted on the edge of the dish to guide the user to an intended target location.

7. The multi-function germicidal station of claim 1, wherein the EDHCNGA comprises an array of parametric ultrasound speakers configured to be modulated with audio signal sources causing body destruction to pathogens and small insects further in the direct path of directional self-demodulated ultrasound and audio beams.

8. The multi-function germicidal station of claim 1, wherein the air delivery elbow comprises an anti-stalled open center turntable to prevent stalling the horizontal sweeping motion motor, wherein a first side of the turntable is attached to a downward direction on the elbow and a second side of turntable is attached to a wire reinforced flexible air duct clamped onto a discharge port of a floor level internal germicidal chamber, and wherein an inside the air delivery elbow is installed an array of parametric ultrasound speakers configured to modulate audio signals facing an oppositely oncoming air upward by a high volume air blower fan, and a resulting ultrasonic wave traveling downward collides with the remnant pathogens refracted to sidewalls and further weakening a strength of the pathogens.

9. The multi-function germicidal station of claim 1, wherein a surface mounted oscillation motion open center turntable connects between an external dish head and a conical nozzle comprising a motor to drive an arm and gearing couples to the dish head causing the dish head to turning in an oscillation motion to reduce pixilation gaps due to focused UV beams.

10. The multi-function germicidal station of claim 1, wherein a ceiling level EDHCNGA is a supply source of air and a floor level intake air filter through a high volume air blower fan is the return source of air and a supply source of pressurized air discharges via a conical shaped nozzle traveling farther away from the germicidal station and dispersing throughout an area of ceiling level for a repeating disinfection via a horizontal sweeping motion motor driving the EDHCNGA across a horizontal plane actively disinfect a large room in shorter time.

11. A multi-function germs intercepting air blasting station comprising:

an active noise cancellation circuitry paired with a microphone and an audio speaker configured to reduce an air blower fan noise;

a multi motion docking assembly supported by an electronic system controller;

a vertical motion linear actuator supported by the electronic system controller and the multi motion docking assembly;

a bow motion linear actuator configured to support a high volume high velocity air blasting cannon;

an oscillation motion open center turntable encircling an air blasting cannon blower tube and attached onto an external foldable blades germicidal assembly; and a blower tube internal germicidal chamber connected to the high volume high velocity air blasting cannon which pushes intake air through the blower tube internal germicidal chamber and discharges toward the oscillating motion open center turntable passing through the external foldable blades germicidal assembly, wherein the high volume high velocity air blasting cannon is seated on the multi motion docking assembly driven by a horizontal sweeping motion motor and activated with the bow motion linear actuator motor directs high velocity air in three dimensions.

12. The multi-function germs intercepting air blasting station of claim 11, wherein the multi motion docking assembly is motor driven with a stationary lower mounting baseboard attached to a top section of a hinge, an upper mount docking plate securely holding the high velocity high volume air blasting cannon in a detachable manner.

13. The multi-function germs intercepting air blasting station of claim 11, wherein a bottom section of a hinge attached to an extendable and retractable supporting rod of the vertical motion linear actuator in a stationary portion is attached to a pole floor stand, and wherein activating a motor of the vertical motion linear actuator causes a raising and a lowering of the high velocity high volume air blasting cannon.

14. The multi-function germs intercepting air blasting station of claim 11, further comprising a bottom section of a hinge jointly connected to a stationary portion of a housing of the bow motion linear actuator, and an extendable and retractable supporting rod of the bow motion linear actuator is pivotally mounted away from a center axes of the hinge onto a lower mounting baseboard of the multi motion docking assembly, wherein a relative pivot distance defines an area to be treated, and the bow motion linear actuator motor causes the multi motion docking assembly to rotate between a clockwise and a counter clockwise direction when laterally observed.

15. The multi-function germs intercepting air blasting station of claim 11, wherein a blower tube internal germicidal chamber comprises an ozone generator module, a hydroxyl generator module, a bipolar ions generator module, a multi wavelength ultraviolet light source module and switching electrostatic charge plates coated with a Titanium Dioxide semiconductor material effecting a photocatalytic oxidation (PCO).

16. The multi-function germs intercepting air blasting station of claim 11, further comprising a blower tube surface mounted external foldable blades germicidal assembly (BTSMEFBGA) comprising a group of multi wavelength zoom and focusable UV LED or laser UV diodes, of wavelength from 200 nm to 400 nm and distributed throughout the foldable blades, wherein the UV LED are zoom and focusable by adjusting a focal point intensity and a light dispersion by a collimator and an optical lens for fast pathogen disinfection; via a motor driven oscillation motion open center turntable attached to the EFBGA (external foldable blades germicidal assembly) causing reduced pixilation gaps due to a group of spreading focused UV beams of 650 nm red laser diodes mounted on tips of the blades to guide a user to their intended target location.

17. The multi-function germs intercepting air blasting station of claim 11, further comprising an external foldable blades germicidal assembly comprising an array of parametric ultrasound speakers modulated with audio signal sources causing body destruction to pathogens and small insects in the direct path of further directional self-demodulated ultrasound and audio beams.

18. The multi-function germs intercepting air blasting station of claim 11, wherein the high velocity high volume air blasting cannon is detachable from the multi motion docking assembly and is hand carried with its own portable battery, internal germicidal chamber and external foldable blades germicidal assembly configured for blasting a person or group of persons to dislodge particulates and pathogens that cling to them for mobilized pathogen disinfection.

19. A method of operating a multi-function germicidal station, comprising:

selecting an internal germicidal chamber and external dish head conical nozzle germicidal assembly for pathogen disinfection and lowering the external dish head conical nozzle germicidal assembly from a ceiling level of a room based on a manually observed or sensor detected no occupant presence in the room, and raising the external dish head conical nozzle germicidal assembly to the predetermined level above a head of an occupant and selecting only an internal germicidal chamber for safe upper room use; and choosing a hydroxyl radical generator, a bipolar ions generator, a multi wavelength ultraviolet light source and electrostatic charge plates coated with a Titanium Dioxide semiconductor material module effecting photocatalytic oxidation (PCO) and parametric ultrasound speakers, based on an occupancy of the room and both of the internal germicidal chamber and the external dish head conical nozzle germicidal assembly can be selected for fast acting disinfection.

20. The method of operating the multi-function germicidal station of claim 19, further comprising:

selecting the internal germicidal chamber and an external foldable blades germicidal assembly, to keep hitchhiked pathogens outside of a house via an air blasting station ideally placing at a door entrance facing an outside direction for blasting an occupant from head to feet prior to admitting the occupant inside a house;

accelerating ozone and hydroxyl molecules at high momentum via the air blasting station configured for dislodging hitchhiked pathogens and particulates clung to occupants therein; and detaching a high velocity high volume air blasting cannon from the germs intercepting air blasting station into a portable handheld long reach germicidal fogger without use of liquid disinfectant via the internal germicidal chamber and external foldable blades germicidal assembly to speedily disinfect the house.

* * * * *